United States Patent
Cai (10) Patent No.: US 8,591,421 B2
(45) Date of Patent: Nov. 26, 2013

(54) SYSTEMS AND METHODS FOR MAKING AND USING ROTATIONAL TRANSDUCERS FOR CONCURRENTLY IMAGING BLOOD FLOW AND TISSUE

(75) Inventor: Anming He Cai, San Jose, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 141 days.

(21) Appl. No.: 13/239,124

(22) Filed: Sep. 21, 2011

(65) Prior Publication Data

US 2012/0123271 A1 May 17, 2012

Related U.S. Application Data

(60) Provisional application No. 61/412,945, filed on Nov. 12, 2010.

(51) Int. Cl.
  *A61B 8/14* (2006.01)
(52) U.S. Cl.
  USPC .......................... 600/459; 600/407; 600/437
(58) Field of Classification Search
  None
  See application file for complete search history.

(56) References Cited

U.S. PATENT DOCUMENTS

| | | | |
|---|---|---|---|
| 6,945,938 B2 | 9/2005 | Grunwald | |
| 7,246,959 B2 | 7/2007 | Nakatani | |
| 7,306,561 B2 | 12/2007 | Sathyanarayana | |
| 2001/0017937 A1* | 8/2001 | Bonnefous | 382/128 |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |

FOREIGN PATENT DOCUMENTS

| | | |
|---|---|---|
| EP | 0797106 A2 | 9/1997 |
| EP | 1690497 A1 | 8/2006 |
| WO | 95/29633 A1 | 11/1995 |
| WO | 2009/105616 A2 | 8/2009 |

OTHER PUBLICATIONS

International Search Report and Written Opinion for International Patent Application PCT/US2011/052650 mailed Jan. 31, 2012.

\* cited by examiner

*Primary Examiner* — Unsu Jung
*Assistant Examiner* — Saurel J Selkin
(74) *Attorney, Agent, or Firm* — Frommer Lawrence & Haug LLP; Patrick R. Turner (57) ABSTRACT

A method for generating a composite image using an intravascular imaging device includes receiving reflected echo signals from at least one transducer along a first of a plurality of radial scan lines. The received echo signals are passed through a plurality of signal processing channels to form a plurality of filtered signals. The filtered signals include a high-resolution tissue structure signal and at least one first pre-blood-flow-mask signal. High-resolution tissue structure signals are processed to form a high-resolution tissue structural image. First pre-blood-flow-mask signals are cross-correlated with second pre-blood-flow-mask signals from an adjacent radial scan line to form blood-flow-mask signals. Blood-flow-mask signals are processed to form a blood-flow mask. For each pixel of the composite image, it is determined whether to use a corresponding pixel of the high-resolution tissue structural image or a corresponding pixel of the cross-correlated blood flow mask to generate the composite image pixel.

20 Claims, 9 Drawing Sheets

SYSTEMS AND METHODS FOR MAKING AND USING ROTATIONAL TRANSDUCERS FOR CONCURRENTLY IMAGING BLOOD FLOW AND TISSUE

CROSS-REFERENCE TO RELATED APPLICATIONS

This application claims the benefit under 35 U.S.C. §119 (e) of U.S. Provisional Patent Application Ser. No. 61/412,945 filed on Nov. 12, 2010, which is incorporated herein by reference.

TECHNICAL FIELD

The present invention is directed to the area of imaging systems that are insertable into a patient and methods of making and using the imaging systems. The present invention is also directed to imaging systems with rotational transducers configured and arranged for concurrently imaging both patient tissue and blood flow and combining the images to form composite images, as well as methods of making and using the rotatable transducers and imaging systems.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (With a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiment, a method for generating a composite image using an intravascular imaging device, the composite image including a plurality of pixels, includes inserting an imaging device into a blood vessel of a patient. The imaging device is coupled to a processor. The imaging device includes at least one transducer disposed in a lumen defined in a sheath. The at least one transducer is configured and arranged for transforming applied electrical signals to acoustic signals. The acoustic signals are transmitted along a plurality of radial scan lines by the at least one transducer as the at least one transducer rotates about a longitudinal axis of the sheath. Reflected echo signals are received by the at least one transducer along a first radial scan line of the plurality of radial scan lines. The echo signals correspond to the transmitted acoustic signals. The received echo signals are passed through a plurality of signal processing channels each including a first filter to form a plurality of filtered signals. The plurality of filtered signals includes a first high-resolution tissue structure signal, a first blood-flow signal, and a first low-resolution tissue structure image signal. The first high-resolution tissue structure signal and a plurality of second high-resolution tissue structure signals received from additional radial scan lines of the plurality of radial scan lines are processed to generate a high-resolution tissue structural image. The first blood-flow signal and the first low-resolution tissue structure image signal are processed with a plurality of second blood-flow signals received from additional radial scan lines of the plurality of radial scan lines to generate a blood-flow image that includes at least one of a blood-flow velocity image, a blood-flow energy image, or a low-resolution structural energy image. For each pixel of the composite image, it is determined whether to use a corresponding pixel of the high-resolution tissue structural image or a corresponding pixel of the blood-flow image to generate the composite image pixel.

In another embodiment, a computer-readable medium having processor-executable instructions for reading data from a processor in communication with at least one transducer disposed in a catheter, the processor-executable instructions when installed on a device enable the device to perform actions, includes receiving reflected echo signals. The echo signals correspond to acoustic signals transmitted from the at least one transducer along each of a plurality of radial scan lines as the at least one transducer rotates about a longitudinal axis of the catheter. The received echo signals are passed through a plurality of signal processing channels each including a first filter to form a plurality of filtered signals. The plurality of filtered signals includes a first high-resolution tissue structure signal, a first blood-flow signal, and a first low-resolution tissue structure image signal. The first high-resolution tissue structure signal and a plurality of second high-resolution tissue structure signals received from additional radial scan lines of the plurality of radial scan lines are processed to generate a high-resolution tissue structural image. The first blood-flow signal and the first low-resolution tissue structure image signal are processed with a plurality of second blood-flow signals received from additional radial scan lines of the plurality of radial scan lines to generate a blood-flow image that includes at least one of a blood-flow velocity image, a blood-flow energy image, or a low-resolution structural energy image. For each pixel of the composite image, it is determined whether to use a corresponding pixel of the high-resolution tissue structural image or a corresponding pixel of the blood-flow image to generate the composite image pixel.

In yet another embodiment, a catheter-based imager includes at least one transducer insertable into a catheter at least partially insertable into a patient. The at least one transducer is coupled to a control module. A processor is in communication with the control module. The processor executes processor-readable instructions that enable actions, including receiving reflected echo signals that correspond to acoustic signals transmitted from the at least one transducer along each of a plurality of radial scan lines as the at least one transducer rotates about a longitudinal axis of the catheter. The received echo signals are passed through a plurality of signal processing channels each including a first filter to form a plurality of filtered signals. The plurality of filtered signals includes a first high-resolution tissue structure signal, a first blood-flow signal, and a first low-resolution tissue structure image signal. The first high-resolution tissue structure signal and a plurality of second high-resolution tissue structure signals received from additional radial scan lines of the plurality of radial scan lines are processed to generate a high-resolution tissue structural image. The first blood-flow signal and the first low-resolution tissue structure image signal are processed with a plurality of second blood-flow signals received from additional radial scan lines of the plurality of radial scan lines to generate a blood-flow image that includes at least one of a blood-flow velocity image, a blood-flow energy image, or a low-resolution structural energy image. For each pixel of the composite image, it is determined whether to use a corresponding pixel of the high-resolution tissue structural image or a corresponding pixel of the blood-flow image to generate the composite image pixel.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of imaging systems that are insertable into a patient and methods of making and using the imaging systems. The present invention is also directed to imaging systems with rotational transducers configured and arranged for concurrently imaging both patient tissue and blood flow and combining the images to form composite images, as well as methods of making and using the rotatable transducers and imaging systems.

The methods, systems, and devices described herein may be embodied in many different forms and should not be construed as limited to the embodiments set forth herein. Accordingly, the methods, systems; and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 2006/0100522; 2006/0106320; 2006/0173350; 2006/0253028; 2007/0016054; and 2007/0038111; all of which are incorporated herein by reference.

Figure 1:
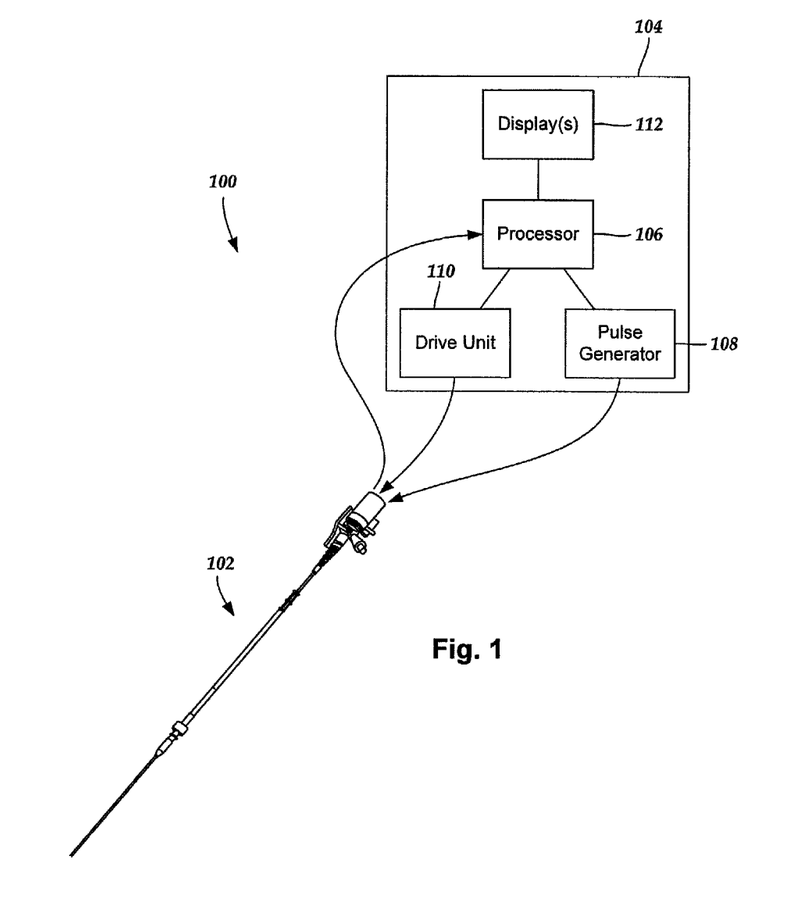
FIG. 1 is a schematic view of one embodiment of an ultrasound imaging system suitable for insertion into a patient, the ultrasound imaging system including a catheter and a control module, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric pulses that may be input to one or more transducers (312 in FIG. 3) disposed in the catheter 102.

In at least some embodiments, mechanical energy from the drive unit 110 may be used to drive an imaging core (306 in FIG. 3) disposed in the catheter 102. In at least some embodiments, electric signals transmitted from the one or more transducers (312 in FIG. 3) may be input to the processor 106 for processing. In at least some embodiments, the processed electric signals from the one or more transducers (312 in FIG. 3) can be displayed as one or more images on the one or more displays 112. For example, a scan converter can be used to map scan line samples (e.g., radial scan line samples, or the like) to a two-dimensional Cartesian grid to display the one or more images on the one or more displays 112.

In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
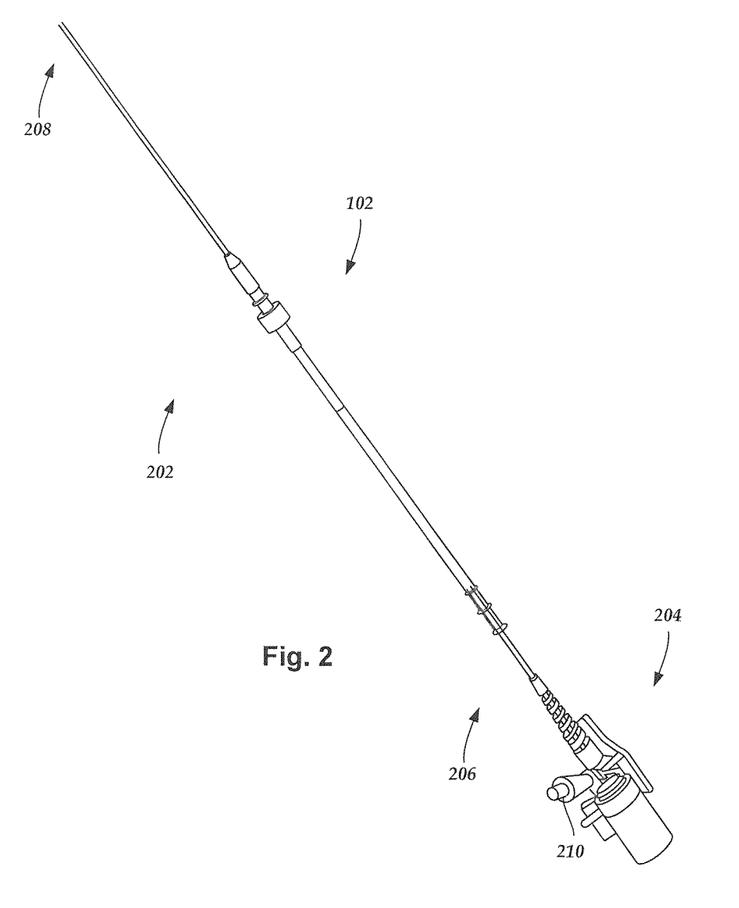
FIG. 2 is a schematic side view of one embodiment of the catheter of FIG. 1, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2 the proximal end 206 of the elongated member 202 is coupled to the catheter hub 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
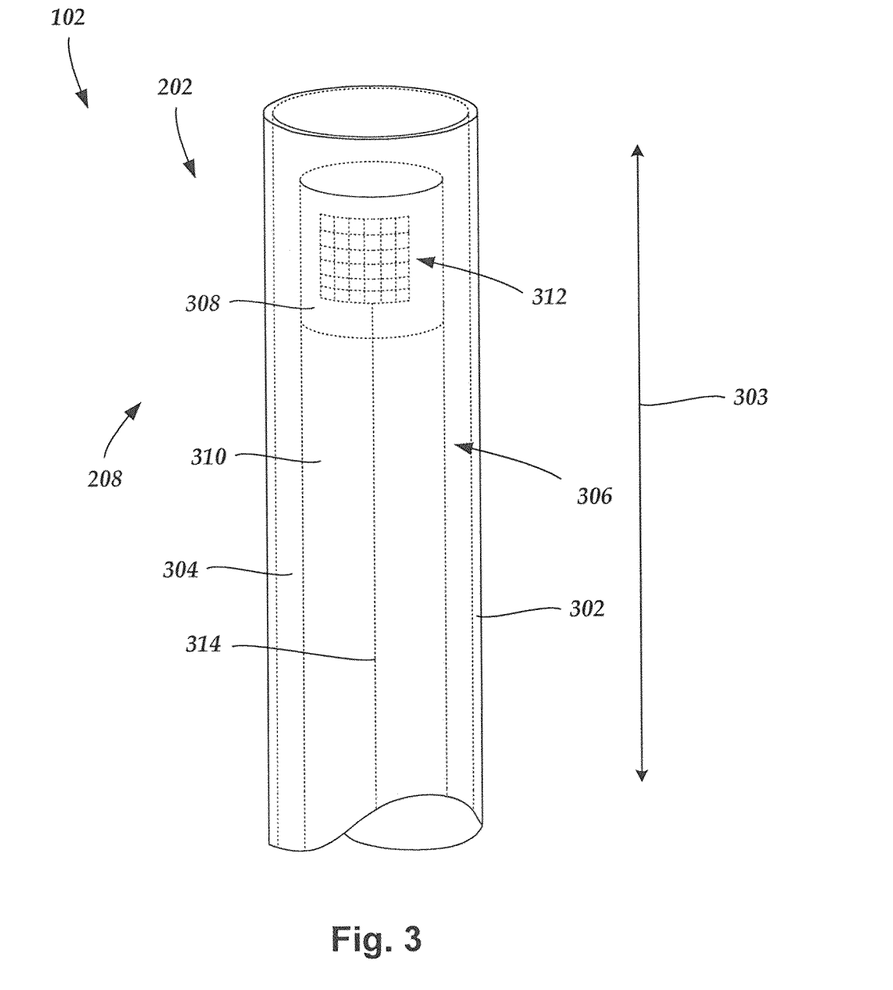
FIG. 3 is a schematic longitudinal cross-sectional view of one embodiment of a distal end of the catheter of FIG. 1 with an imaging core disposed in a lumen defined in a sheath, according to the invention.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 coupled to a distal end of a driveshaft 310 that is rotatable either manually or electronically. One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane; plastic, spiral-cut stainless steel, nitinol hypotube, and the like or combinations thereof.

In a preferred embodiment (as shown in FIG. 3), an array of transducers 312 are mounted to the imaging device 308. In alternate embodiments, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 is employed, the transducers 312 can be configured into any suitable arrangement including, for example, an annular arrangement, a rectangular arrangement, or the like.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like)

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 may, optionally, be rotated about the longitudinal axis 303 of the catheter 102. As the imaging core 306 rotates, the one or more transducers 312 emit acoustic signals in different radial directions (i.e., along different radial scan lines). For example, the one or more transducers 312 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the drive unit 110 disposed in the control module (104 in FIG. 1). In alternate embodiments, the one or more transducers 312 are fixed in place and do not rotate. In which case, the driveshaft 310 may, instead, rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image (e.g., a tomographic image) of a portion of the region surrounding the one or more transducers 312, such as the walls of a blood vessel of interest and tissue surrounding the blood vessel. The radial cross-sectional image can, optionally, be displayed on one or more displays 112. The at least one of the imaging core 306 can be either electronically or manually rotated.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (i.e., pulled back) along the longitudinal length of the catheter 102. The catheter 102 can include at least one telescoping section that can be retracted during pullback of the one or more transducers 312. In at least some embodiments, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

When the imaging core 306 is retracted while rotating, the images may collectively form a continuous spiral shape along a blood vessel. A stepper motor may, optionally, be used to pull back the imaging core 306. The stepper motor can pull back the imaging core 306 a short distance and stop long enough for the one or more transducers 306 to capture an image before pulling back the imaging core 306 another short distance and again capturing another image, and so on, either with or without being rotated.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 100 MHz.

One or more conductors 314 can electrically couple the transducers 312 to the control module 104 (see e.g., FIG. 1). In which case, the one or more conductors 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

Figure 4:
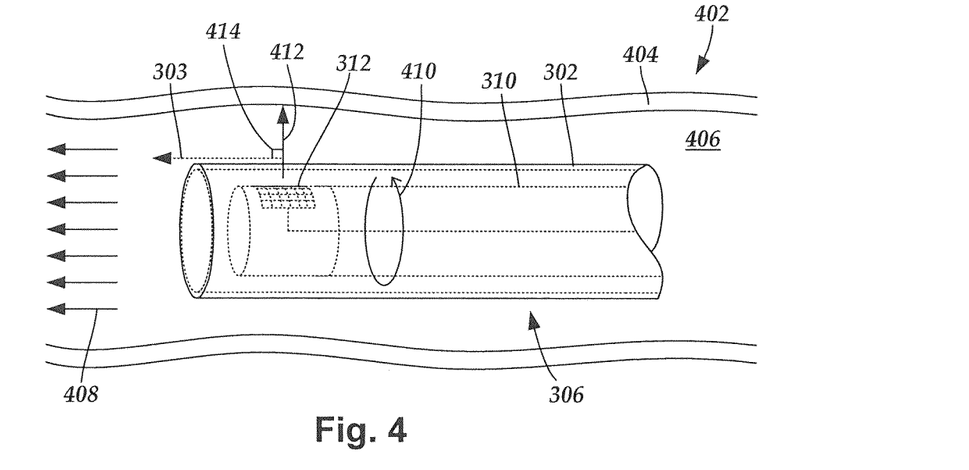
FIG. 4 is a schematic side view of one embodiment of a distal end of the imaging core and sheath of FIG. 3 disposed in a blood vessel, the imaging core configured and arranged to image in a direction that is roughly perpendicular to a longitudinal axis of the sheath, according to the invention.

When imaging patient tissue, such as blood vessel walls and surrounding tissue and structures, it may be advantageous to form the imaging device 308 such that the one or more transducers 312 direct acoustic signals in a direction that is roughly perpendicular to the longitudinal axis 303 of the sheath 302. FIG. 4 is a schematic side view of one embodiment of a distal end of the imaging core 306 disposed in the sheath 302 which, in turn, is disposed in a blood vessel 402. The blood vessel 402 includes a wall 404 and a lumen 406 within which the sheath 302 and imaging core 306 are disposed. Blood flow within the lumen 406 of the blood vessel 402 is generally in the direction shown by arrows 408. In some cases, the blood flow may be generally in a direction that is opposite to the direction of the arrows 408.

The longitudinal axis 303 of the sheath 302 is generally parallel with the blood vessel lumen 406. The driveshaft 310 is configured and arranged to rotate about the longitudinal axis 303 of the sheath 302, as shown by arrow 410. As shown in FIG. 4, the one or more transducers 312 are side-facing. In other words, a face of the one or more transducers 312 is oriented such that the normal line of the face is in a direction 412 that is roughly perpendicular 414 to the longitudinal axis 303 of the sheath 302. Thus, the one or more transducers 312 are disposed at an angle that is often conducive to imaging patient tissue, such as the blood vessel wall 404, from within the lumen 406 of the blood vessel 402. The one or more transducers 312 can be rotated about the longitudinal axis 303 of the sheath 302, as shown by arrow 410, while transmitting and receiving acoustic signals along a plurality of radial scan lines.

In addition to, or in lieu of, imaging patient tissue, the IVUS system 100 can be used as a diagnostic tool to measure blood flow within the blood vessel 402. When acoustic signals from the one or more transducers 312 reflect off of moving objects, such as red blood cells flowing along the lumen 406 of the blood vessel 402, a Doppler frequency shift may occur that can be distinguished from stationary objects (e.g., the blood vessel wall 404, tissue that is external to the blood vessel 402, stationary structures within the blood vessel 402, such as blood or plaque, or the like).

At least some conventional IVUS systems visualize blood flow through continuous or repeated acoustic-signal transmissions along a fixed position and orientation (i.e., along a single radial scan line). For example, the transducer can be facing forward from a distal tip of a sheath such that acoustic signals propagate along an angle that is parallel with a longitudinal axis of a sheath. A Doppler frequency or phase shift can be derived from the corresponding received echo signals along the fixed radial scan line. When a single radial scan line is continuously imaged, the resultant Doppler shift can be displayed as a velocity trace along the radial scan line. When this imaging process is repeated, the resultant two-dimensional blood-flow velocity (or blood-flow energy) can be displayed.

Side-facing transducers (see FIG. 4) are not typically used to visualizing blood flow because blood flow is generally perpendicular to the direction of acoustic-signal transmission from a side-facing transducer. At least some conventional IVUS systems, however, image both patient tissue and visualize blood flow by including one or more forward-facing Doppler transducers and one or more separate side-facing transducers for imaging tissue (e.g., blood vessel walls, or the like). Employing both one or more forward-facing Doppler transducers and one or more side-facing transducers enables a composite image to be formed that combines information from both sets of imagers. For example, the received signals from the forward-facing transducer(s) can be used to form a Doppler strip that can be concurrently displayed with a two-dimensional structural gray image acquired with the side-facing transducer(s). In some instances, blood flow imaging and tissue imaging can be performed separately using the same transducer(s).

Rotating transducers are not commonly used to visualize blood flow. When transducers are continually rotating during an imaging procedure, acoustic-signal transmissions are most likely not consistently along the exact same radial scan line of acoustic signal transmission. Imaging from inconsistently-positioned radial scan lines may cause the formation of undesired motion artifacts. Accordingly, it would be advantageous to develop a processing method to reduce motion artifacts generated during Doppler imaging using one or more rotating transducers.

As herein described, the IVUS imaging system 100 with the one or more rotatable transducers 312 can be used concurrently to provide a cross-sectional image of patient structures (e.g., the blood vessel wall 404, and the like) and also to visualize blood flow within the blood vessel lumen 406. Optionally, a composite image (e.g., cross-sectional, longitudinal, or the like) can be formed from the structural image and the visualized blood flow (e.g., a blood-flow image). Additionally, a processing method can be used with the IVUS imaging system 100 to reduce motion artifacts potentially generated from using one or more rotating transducers to visualize blood flow. In at least some embodiment, the processing method can include transmission of multiple acoustic signals from the one or more rotatable transducers 312 along individual radial scan lines. In at least some embodiments, the rate of rotation of the transducer is reduced to increase the amount of overlap of adjacent radial scan lines. In at least some embodiments, the frequency of the acoustic signals transmitted from the transducer is reduced to enable the amount of time between successive transmissions of acoustic signals to be increased for slower flow.

In at least some embodiments, received echo signals are passed through signal processing channels to extract different information. The output signals from each of the different signal processing channels can be used to generate a high-resolution structural image or a blood-flow image that indicates the presence of flowing blood. The blood-flow image may include one or more blood-flow energy images or one or more blood-flow velocity images, or both. In at least some embodiments, the blood-flow mask includes an accompanying low-resolution structural energy image. The blood-flow image can be combined with the high-resolution structural image to form a composite image.

Figure 5:
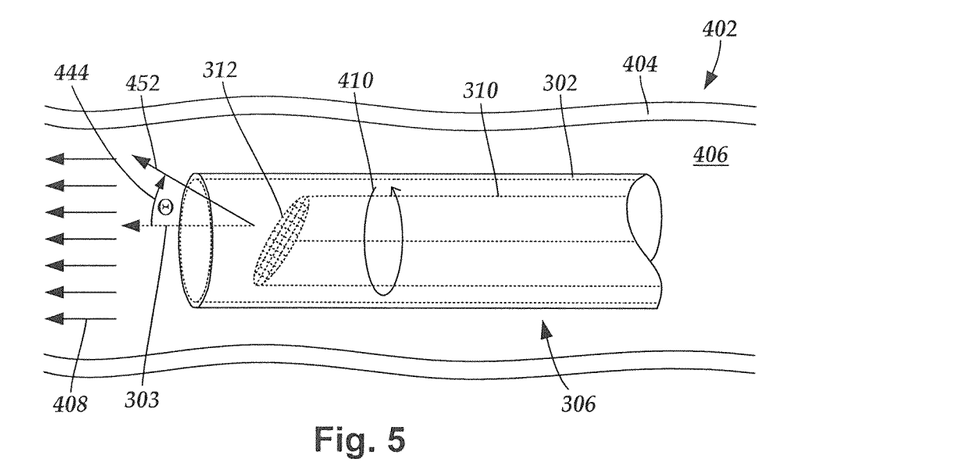
FIG. 5 is a schematic side view of one embodiment of a distal end of the imaging core and sheath of FIG. 3 disposed in a blood vessel, the imaging core configured and arranged to image in a direction that is neither parallel nor perpendicular to a longitudinal axis of the sheath, according to the invention.

In order to detect both blood flow and tissue information, it may be beneficial to tilt the one or more transducers 312 relative to the sheath 302 such that acoustic signals are transmitted in a direction that is not perpendicular to either the blood vessel wall 404 or the direction of general blood flow 408. FIG. 5 is a schematic side view of one embodiment of a distal end of the imaging core 306 disposed in the sheath 302 which, in turn, is disposed in the blood vessel 402. The one or more transducers 312 are tilted in relation to the longitudinal axis 303 of the sheath 302 such that a face of the one or more transducers 312 is oriented such that the normal line 452 of the face is in a direction that is at an angle Θ 444 with the longitudinal axis 303 of the sheath 302, where the angle Θ 444 is greater than zero degrees and less than ninety degrees. The angle Θ 444 can be between, for example, 5° and 85°, 10° and 80°, 15° and 75°, 20° and 70°, 25° and 65°, 30° and 60°, 35° and 55°, 40° and 50°.

In FIG. 5, the normal line 452 is shown in a side/forward direction. In alternate embodiments, the normal line 452 can be oriented in a side/rearward direction, such that the angle Θ 444 is greater than ninety degrees and less than one hundred eighty degrees with the longitudinal axis 303 of the sheath 302. In which case, the angle Θ 454 can be between, for example, 95° and 175°, 100° and 170°, 105 and 165°, 110° and 160°, 115° and 155°, 120° and 150°, 125° and 145°, 130° and 140°.

When a blood flow velocity v is parallel to the longitudinal axis 303 of the sheath 302, a pure tone acoustic wave with frequency $f_0$ can be reflected from the blood flow with a tone shift $$\Delta f = \frac{f_0 v \cos\theta}{c},$$

where c is the speed of sound in blood. When two identical acoustic signals with center frequency $f_0$ and a bandwidth that is a fraction of $f_0$ are transmitted from the one or more transducers 312 with time separation Δt, the corresponding received echo signals have the phase difference, $$\Delta\phi = 2\pi \cdot \frac{f_0 \Delta t \cdot v \cos\theta}{c}.$$

Thus, phase shift is a function of both the frequency of the transmitted acoustic signals and the time separation between transmission of acoustic signals. Accordingly, one or more of the frequency of the transmitted acoustic signals and the time separation between transmissions of the acoustic signals can be adjusted to form images with variation in phase shift that does not exceed $2\pi$. It is advantageous to prevent the phase shift from exceeding $2\pi$ in order to maintain a one-to-one correlation between phase shift and velocity.

Typically, when rotatable transducers 312 are used for imaging structures (e.g., the blood vessel wall 404), multiple transmit/receive acoustic signals are propagating to and from the transducers 312 in different directions (i.e., along different radial scan lines) as the one or more transducers 312 rotate about the longitudinal axis 303 of the sheath 302. In some cases, even though the multiple transmit/receive acoustic signals may be pointing in different directions, neighboring transmit/receive acoustic signals can have a significant amount of overlap. As discussed above, the amount of overlap may be controllable by adjusting the rotational speed of the transducers 312, the frequency of the acoustic signals output by the transducers 312, or the like. Thus, blood-flow imaging may be achievable using the rotatable transducers 312 by using an appropriate combination of time intervals between consecutive radial-signal-line transmissions and acoustic-signal spatial overlap between adjacent radial scan lines.

When imaging flowing blood, the time intervals between a first acoustic signal transmission along a first radial scan line and a second acoustic signal transmission along an adjacent radial scan line is typically much longer than the time it takes for the first acoustic signal to be transmitted from the transducer, reflect off of a red blood cell, and be received as an echo signal by the transducer. Accordingly, in at least some embodiments, multiple first acoustic-signal transmissions can be combined along a first radial scan line to form a single vector, and the phase shift can be calculated with one or more second acoustic-signal transmissions acquired $\Delta t$ time later along a second radial scan line.

Echo signals received along a radial scan line can be passed along a plurality of different signal processing channels. The groups of echo signals can be received as a result of a single acoustic-signal transmission along a given radial scan line. Alternatively, the groups of echo signals can be received as a result of separate acoustic-signal transmissions along a given radial scan line. The plurality of different signal processing channels can each be used to extract different information from the echo signals obtained along the radial scan line. The extracted information can be used to form one or more displayable images. For example, the plurality of different signal processing channels can each be used to separately extract information from echo signals to form signals used to generate a high-resolution structural image and a blood-flow image that can be combined with the high-resolution structural image to form a composite image. The blood-flow image may be formed using signals that include one or more of blood-flow energy information, blood-flow velocity information, or low-resolution structural information.

The extracted information from the received echo signals can be combined into one or more composite images in any suitable combination. The blood-flow image can, optionally, be limited in the composite image such that individual pixels of the blood-flow image are only displayed when those pixels exceed one or more threshold energy values. The one or more threshold energy levels can be predetermined values, or can be user-defined, or both.

Figure 6:
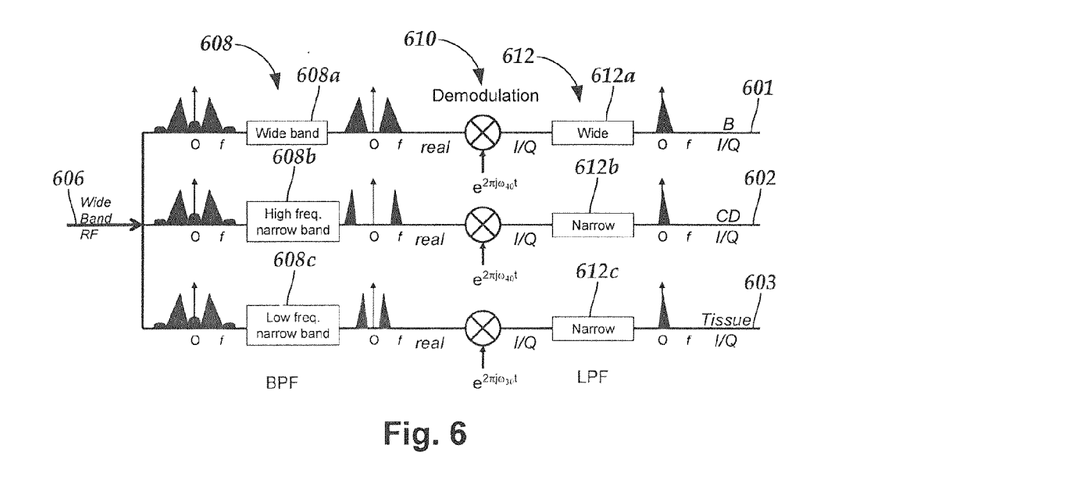
FIG. 6 is a schematic view of one embodiment of signal processing channels configured and arranged to extract different information from echo signals received along a radial scan line, the channels forming a high-resolution structural image signal, a blood-flow signal, and a low-resolution structural image signal that enhances non-blood-flow structures, according to the invention.

FIG. 6 is a schematic view of one embodiment of three different signal processing channels 601-603 that can be used to extract different information from input echo signals 606 received along a radial scan line. The received echo signals 606 can be from acoustic signals transmitted concurrently, or sequentially, along the radial scan line. When the received echo signals 606 are transmitted along the signal processing channels 601-603, the echo signals 606 are passed through a bandpass filter 608, demodulated 610, and passed through a lowpass filter 612.

in FIG. 6, the signal processing channel 601 extracts high-resolution structural information by passing the echo signals 606 through a wideband bandpass filter 608a and a wideband lowpass filter 612a. Thus, the output signal of signal processing channel 601 can be combined with similarly-processed high-resolution structural signals from other radial scan lines to form a high-resolution structural image.

The signal processing channel 602 extracts blood-flow information by passing the echo signal 606b through a high-frequency; narrowband bandpass filter 608b and a narrow-band lowpass filter 612b. Thus, the output signal of signal processing channel 602 can be further processed and used to form a blood-flow image. The signal processing channel 603 extracts low-resolution structural tissue information by passing the echo signal 606c through a low-frequency, narrow-band bandpass filter 608c and a narrowband lowpass filter 612c. Thus, the output signal of signal processing channel 603 can be further processed and used to form a low-resolution structural image that can be used in the blood-flow image as a companion to the signal output of signal processing channel 602.

Figure 7:
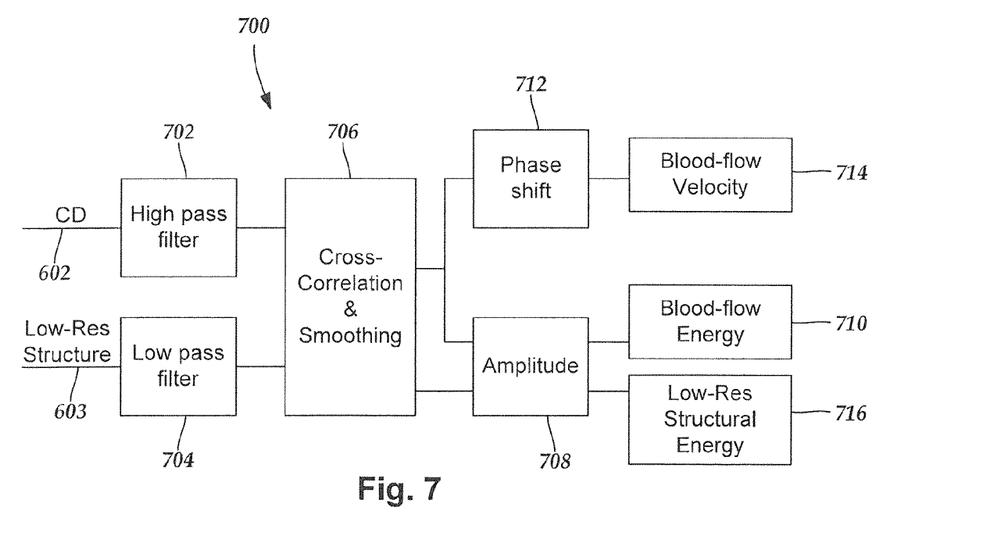
FIG. 7 is a schematic view of one embodiment of signal processing channels for further processing the input blood-flow signal and the low-resolution structural image signal of FIG. 6 with multiple blood-flow signals generated along adjacent radial scan lines to generate blood-flow images that include a blood-flow velocity image based on the phase differences of the blood-flow signal, a blood-flow energy image based on the amplitude of the blood-flow-energy signal, and an accompanying low-resolution structural energy image based on the amplitude of the low resolution structural image signal, according to the invention.

Turning to FIG. 7, the signals output from the signal processing channels 602 and 603 can be combined with signals output from other radial scan lines and further processed into blood-flow images. FIG. 7 is a schematic view of one embodiment of signals 602 and 603 being input to a signal processor 700 for generating blood-flow images, such as blood-flow energy images 710, blood-flow velocity images 714, and low-resolution structural energy images 716. Input signals 602 and 603 can be combined, in various combinations, with similarly-processed signals from other radial scan lines to form blood-flow images which, in turn, can be used in forming a composite image along with a high-resolution structural image.

In FIG. 7, a highpass filter 702 is applied to the signal 602 to reduce visualization of stationary structures, and a lowpass filter 704 is applied to the signal 603 to reduce visualization of blood flow. Optionally, the filters 702 and 704 can be dependent of radial depth. In at least some embodiments, the filters 702 and 704 are across radial scan lines for the same depth samples. The filters 702 and 704 can also be designed to compensate for acoustic beam variation due to rotation. A cross-correlation coefficient 706 is calculated for the signals 602, 603. The cross-correlation coefficient 706 is based on information obtained along adjacent radial scan lines and separated by a desired time interval $\Delta t$. The cross-correlation coefficient 706 can be calculated, in part, through point-by-point multiplication of data points with their corresponding complex conjugates. In at least some embodiments, a noise reduction algorithm may be implemented (e.g., two-dimensional smoothing, or the like). The amplitude 708 of the cross-correlation coefficient 706 is used to generate the blood-flow energy image 710, while the phase change (with a proper conversion factor) 712 between information obtained along adjacent radial scan lines is used to generate the blood-flow velocity image 714. The companion low-resolution structural energy image 716 may be generated from the same amplitude processing block 708 to match radial resolution and angular location.

Figure 8:
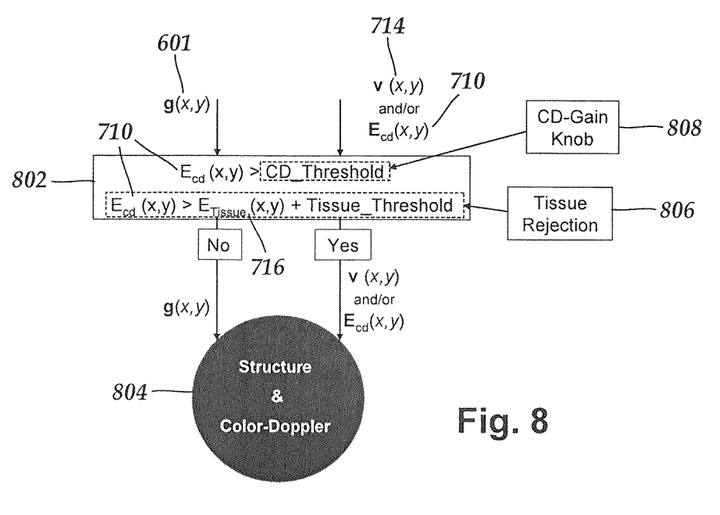
FIG. 8 is a schematic view of one embodiment of a technique for determining whether for each pixel of a composite image, that pixel is to be displayed as a high-resolution structural image pixel or a blood-flow image pixel based on a determination of whether or not blood flow is present in a corresponding pixel of a blood flow mask, the blood flow mask generated based on the blood-flow energy image and the accompanying low-resolution structural energy image of FIG. 7, according to the invention.

Turning to FIG. 8, once a high-resolution structural image and a blood-flow image are both obtained, the images are used to generate a composite image. For each pixel of the composite image it is determined whether to use the corresponding pixel of the high-resolution structural image or the corresponding pixel of the blood-flow image.

In at least some embodiments, a blood-flow mask is generated based on an input blood-flow energy image and accompanying low-resolution structural energy image. For each pixel of the blood-flow image, it is determined whether or not blood flow is present. In at least some embodiments, the blood-flow mask can be thought of as a binary image, where each pixel has a "1" value indicating the presence of blood flow, or a "0" value indicating the absence of blood flow. Accordingly, for each pixel of the composite image, the blood-flow mask will either have a "1" value, indicating the presence of blood flow in the pixel, or a "0" value, indicating absence of blood flow in the pixel. For all the pixels with a "0" value in the blood-flow mask, the composite image includes only the high resolution structural image pixel, while all the other pixels includes only the blood-flow image pixel, or a combined image pixel that includes both the high-resolution structural image pixel and the blood-flow image pixel.

FIG. 8 is a schematic view of one embodiment of a technique for generating a blood-flow mask based on an input blood-flow energy image and accompanying low-resolution structural image signal, and using the blood-flow mask and the high-resolution structural image to generate a composite image. In FIG. 8, for a given pixel of a composite image, signals related to corresponding pixels of the images 601, 710, and 714 are input to a pixel selector 802.

The pixel selector 802 uses a tissue rejecter 806 to determine whether or not blood flow is present in a given pixel. When blood flow is detected (e.g., a "1" value), the input blood-flow image pixel is output. Otherwise, the pixel of the high-resolution structural image is output. In at least some embodiments, when blood flow is detected the output signal is a combination of the blood-flow image pixel and the corresponding high-resolution structural image pixel.

in at least some embodiments, the determination of whether or not blood flow is present in a given pixel of the blood-flow mask is based on a level of the signals 710, 714 (e.g., an energy level, a velocity level, or the like) that is above a pre-determined threshold value. For example, an input blood-flow energy image signal 710 has an energy level above the pre-determined threshold value, or an input blood-flow velocity image signal 714 has a velocity level above the pre-determined threshold value.

When the pixel of the blood-flow image has a level above the threshold level, the pixel of the blood-flow image (e.g., one or more of the blood-flow energy signal, the blood-flow velocity signal, or the low-resolution structural image) is displayed on the composite image and the high-resolution structural signal 601 is rejected. Otherwise, the pixel corresponding to the high-resolution structural signal 601 is displayed. In at least some embodiments, the pixel selector 802 includes a gain selector 808. The gain selector 808 can be used by a user to adjust the pre-determined threshold value.

In at least some embodiments, the structural image is formed in grayscale. In some embodiments, different colors can be used to distinguish different blood-flow velocities or energy levels for overlaying onto the structural image. In preferred embodiments, different color maps are used for velocity and energy displays, with the structural image being displayed in gray levels corresponding to the amplitude of a relatively wideband signal. Any suitable color-coding can be used in conjunction with the blood-flow image. For example, a color-velocity image can color-code blood-flow velocity, a color energy image can color-code blood-flow energy, and color-velocity-energy image can color-code blood-flow velocity, or blood-flow energy, or both.

In at least some embodiments, different transparency levels can be assigned to pixels of the blood-flow image when the blood-flow mask has a "1" value. For example, when the blood-flow mask has a "1" value (indicating the presence of blood flow) for a particular pixel, that pixel can be displayed on the composite image as a combination of colors from the blood-flow image and gray. In at least some embodiments, the transparency levels are user-selected.

Many different variations of composite images are achievable. In at least some embodiments, the angular resolution of the composite image may be improved by performing an aperture synthesis. In at least some embodiments, high velocity and low velocity blood flow can be calculated by combining results from multiple time interval velocities and energy imaging. In at least some embodiments, an A-line Doppler spectrum trace can be displayed. In at least some embodiments, a flow volume calculation can be performed. In at least some embodiments, one or more enhancements (e.g., a lumen enhancement, or the like) can be applied to the structural image.

Figure 9A:
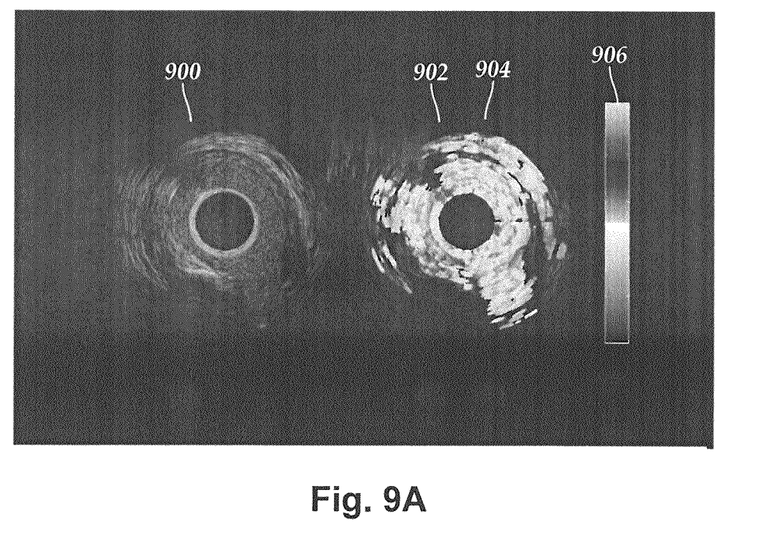
FIG. 9A is a schematic view of one embodiment of a high-resolution structural image and a blood-flow velocity image overlaid onto the high-resolution structural image, according to the invention.

FIGS. 9A-10B show several exemplary combinations of high-resolution structural images and blood-flow images used to form different composite images. The same dataset is used to form each of the images of FIGS. 9A-10B. FIG. 9A is a schematic view of one embodiment of a high-resolution structural image 900 on the left and a composite image 902 on the right. The high-resolution structural image 900 is generated in grayscale. The composite image 902 includes a blood-flow image 904 formed from blood-flow velocity signals. The blood-flow image 904 is generated in color and combined with the high-resolution structural image 900. A key 906 shows the relative velocities of blood flow as different colors. The composite image 902 is formed without using the tissue rejecter 806 of the pixel selector 802.

Figure 9B:
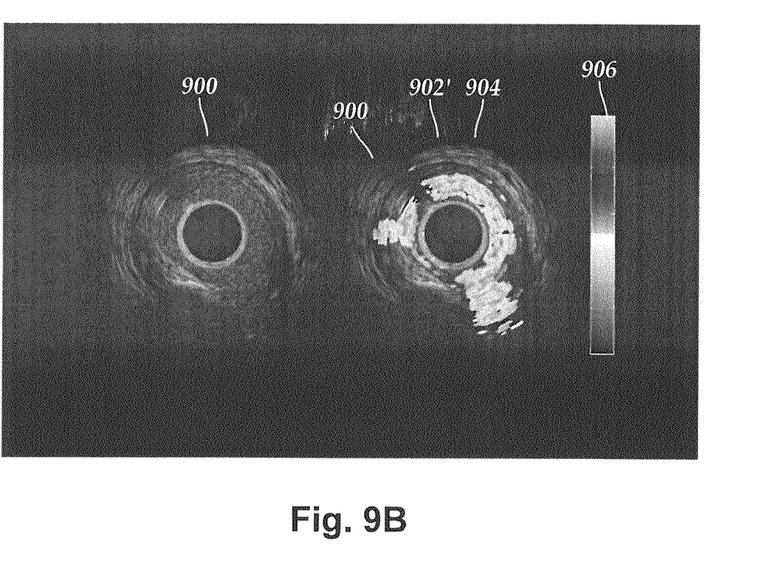
FIG. 9B is a schematic view of one embodiment of the images of FIG. 9A, where pixels of the blood-flow velocity image with zero values in the corresponding blood flow mask are not displayed, according to the invention.

FIG. 9B is a schematic view of one embodiment of the high-resolution structural image 900 on the left and a composite image 902' on the right. The composite image 902' also includes the blood-flow image 904 combined with the high-resolution structural image 900. In FIG. 9B, however, the composite image 902' is formed using the tissue rejecter 806 of the pixel selector 802 to remove pixels of the blood-flow image 904 with "0" values in the blood-flow mask.

Figure 10A:
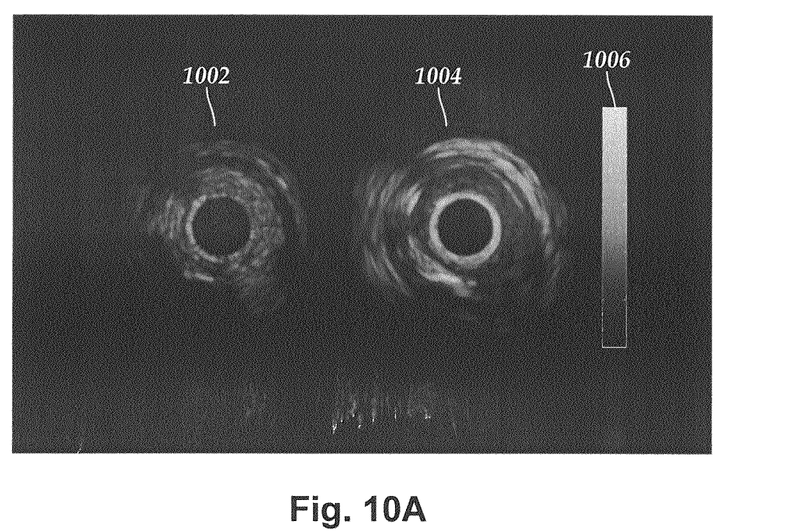
FIG. 10A is a schematic view of one embodiment of a blood-flow energy image and a low-resolution structural energy image, according to the invention.

FIG. 10A is a schematic view of one embodiment of an image 1002 formed from blood-flow energy signals on the left and an image 1004 formed from low-resolution structural energy signals on the right. A key 1006 shows the relative energy strengths as different colors. The images 1002 and 1004 are formed without using the tissue rejecter 806 of the pixel selector 802.

Figure 10B:
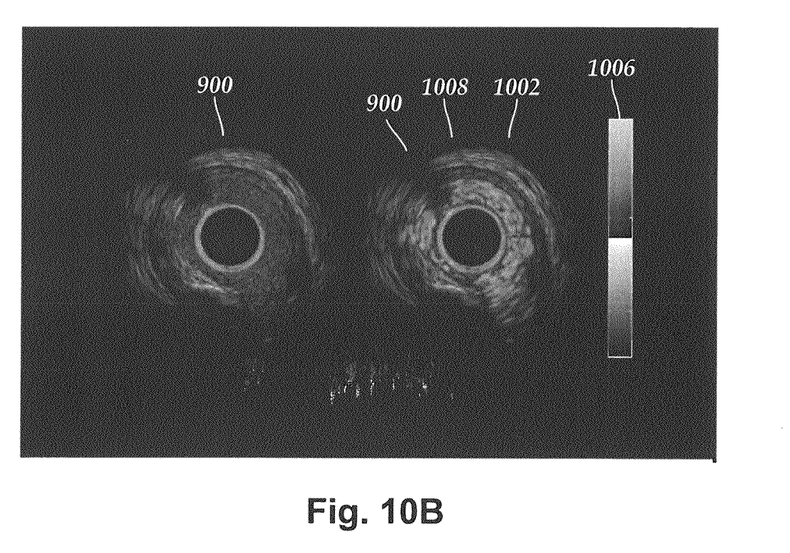
FIG. 10B is a schematic view of one embodiment of the high-resolution structural image of FIG. 9A and a blood-flow image formed from the images of FIG. 10A overlaid onto the high-resolution structural image, where pixels of the blood-flow image with a zero value in the corresponding blood flow mask are not displayed, according to the invention.

FIG. 10B is a schematic view of one embodiment of the high-resolution structural image 900 on the left and a composite image 1008 on the right. The composite image 1008 includes a blood-flow image that includes the images 1002 and 1004 combined with the high-resolution structural image 900. In FIG. 10B, the composite image 1008 is formed using the tissue rejecter 806 of the pixel selector 802 to remove pixels of the blood-flow image with "0" values in the blood-flow mask.

Figure 11:
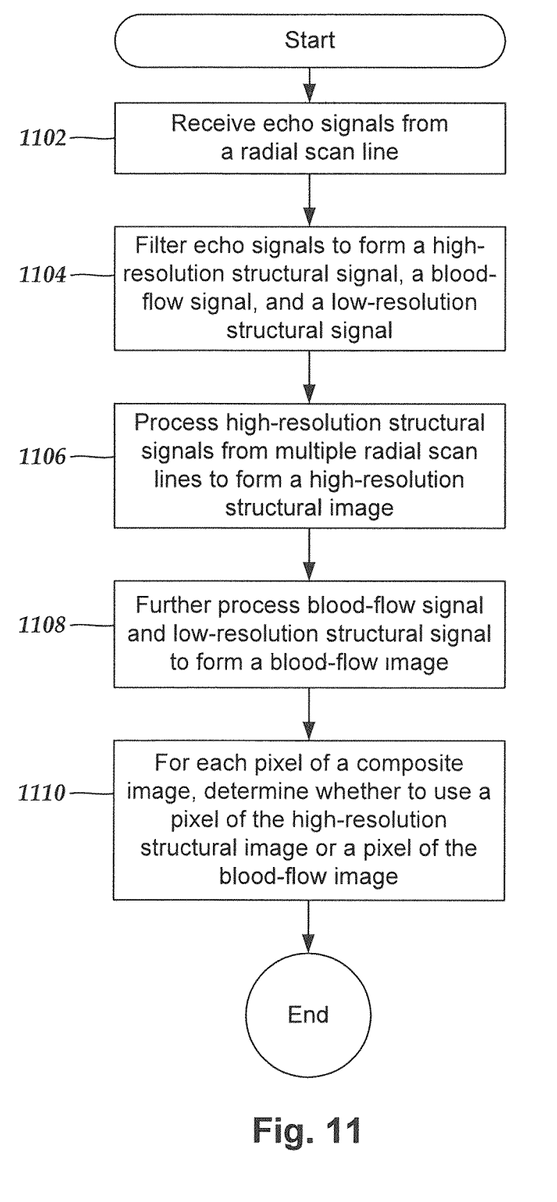
FIG. 11 is a flow diagram of one exemplary embodiment of a signal processing procedure for generating a composite image from echo signals received by a rotating transducer, the composite image including a high-resolution structural image and a blood-flow image, according to the invention.

FIG. 11 is a flow diagram of one exemplary embodiment of a signal processing technique for generating a composite image that includes a blood-flow image combined with a high-resolution structural image formed from the same echo signals received using a rotatable transducer disposed within the blood vessel. The blood-flow image includes one or more of the blood-flow velocity image, the blood-flow energy image, and a low-resolution structural image. In step 1102, echo signals are received from a radial scan line. In step 1104, the received echo signals are passed through a plurality of signal processing channels where the echo signals are filtered to form a high-resolution structural signal, a blood-flow signal, and a low-resolution structural signal. In step 1106, the high-resolution structural signal is combined with high-resolution structural signals from other radial scan lines and processed to form a high-resolution structural image. In step 1108, the blood-flow signal and low-resolution structural signal are further processed to form blood-flow images. In step 1110, for each pixel of a composite image it is determined whether to use a corresponding pixel of the high-resolution structural image or a corresponding pixel of the blood-flow image based on whether or not blood flow is detected in the pixel of the blood-flow image. Optionally, the composite image can be displayed on the one or more displays (112 in FIG. 1).

It will be understood that each block of the flowchart illustrations, and combinations of blocks in the flowchart illustrations, as well any portion of the tissue classifier, imaging transducer(s), control module, systems and methods disclosed herein, can be implemented by computer program instructions. These program instructions may be provided to a processor to produce a machine, such that the instructions, which execute on the processor, create means for implementing the actions specified in the flowchart block or blocks or described for the tissue classifier, imager, control module, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for generating a composite image using an intravascular imaging device, the composite image comprising a plurality of pixels, the method comprising:

inserting an imaging device into a blood vessel of a patient, the imaging device coupled to a processor, the imaging device comprising at least one transducer disposed in a lumen defined in a sheath, the at least one transducer configured and arranged for transforming applied electrical signals to acoustic signals;

transmitting the acoustic signals along a plurality of radial scan lines by the at least one transducer as the at least one transducer rotates about a longitudinal axis of the sheath;

receiving reflected echo signals by the at least one transducer along a first radial scan line of the plurality of radial scan lines, the echo signals corresponding to the transmitted acoustic signals;

passing the received echo signals through a plurality of first signal processing channels to form a plurality of filtered signals, the plurality of filtered signals comprising a first resolution tissue structure signal, a first blood-flow signal, and a second resolution tissue structure image signal, wherein the first resolution tissue structure signal has a resolution that is higher than a resolution of the second resolution tissue structure image signal, wherein each of the plurality of first signal processing channels comprises a different first filter, and wherein each of the received echo signals is passed through each of the different first filters;

processing the first resolution tissue structure signal and a plurality of additional first resolution tissue structure signals received from additional radial scan lines of the plurality of radial scan lines to generate a first resolution tissue structural image;

processing the first blood-flow signal and the second resolution tissue structure image signal with a plurality of additional first blood-flow signals received from additional radial scan lines of the plurality of radial scan lines to generate a blood-flow image that comprises at least one of a blood-flow velocity image, a blood-flow energy image, or a second resolution structural energy image; and combining the first resolution tissue structural image with the blood-flow image to generate a composite image, for each pixel of the composite image, determining whether to use a corresponding pixel of the first resolution tissue structural image or a corresponding pixel of the blood-flow image to generate the composite image pixel.

2. The method of claim 1, further comprising displaying the composite image on at least one display coupled to the processor.

3. The method of claim 1, further comprising inserting the at least one transducer into the lumen of the sheath such that the at least one transducer faces a direction that is neither parallel no perpendicular with the longitudinal axis of the sheath.

4. The method of claim 1, wherein processing the first resolution tissue structure signal and the plurality of additional first resolution tissue structure signals received from additional radial scan lines of the plurality of radial scan lines to generate the first resolution tissue structural image comprises processing the first resolution tissue structure signal and the plurality of additional first resolution tissue structure signals to generate the first resolution tissue structural image in grayscale.

5. The method of claim 1, further comprising applying a different transparency level to the blood-flow image.

6. The method of claim 1, wherein receiving reflected echo signals by the at least one transducer along the first radial scan line of the plurality of radial scan lines comprises sequentially receiving a plurality of sets of reflected echo signals along the first radial scan line, and wherein each set is passed along a different signal processing channel of the plurality of signal processing channels.

7. The method of claim 1, wherein processing the first blood-flow signal and the second resolution tissue structure image signal with the plurality of additional first blood-flow signals to generate the blood-flow image comprises processing the image signals to generate the blood-flow image in color.

8. The method of claim 1, wherein processing the first blood-flow signal and the second resolution tissue structure image signal with a plurality of second blood-flow signals received from additional radial scan lines of the plurality of radial scan lines to generate a blood-flow image comprises passing the first blood-flow signal and the second resolution tissue structure image signal through a second filter.

9. The method of claim 1, wherein processing the first blood-flow signal and the second resolution tissue structure image signal with the plurality of additional first blood-flow signals received from additional radial scan lines of the plurality of radial scan lines to generate the blood-flow velocity image comprises forming the blood-flow velocity image based on the phase difference between the first blood-flow signal of the first radial scan line and at least one of the plurality of second blood-flow signals of at least one radial scan line of the plurality of radial scan lines that is adjacent to the first radial scan line.

10. The method of claim 9, further comprising adjusting an amount of time between successive transmissions of the acoustic signals to adjust the phase difference between the first blood-flow signal of the first radial scan line and a second blood-flow signal of at least one radial scan line of the plurality of radial scan lines that is adjacent to the first radial scan line.

11. The method of claim 1, wherein processing the first blood-flow signal and the second resolution tissue structure image signal with the plurality of additional first blood-flow signals received from additional radial scan lines of the plurality of radial scan lines to generate the blood-flow energy image and the second resolution structural energy image comprises generating the blood-flow energy image and the second resolution structural energy image based, at least in part, on an amplitude of a calculated cross-correlation coefficient.

12. The method of claim 11, wherein determining whether to use a corresponding pixel of the first resolution tissue structural image or a corresponding pixel of the blood-flow image to generate the composite image pixel comprises generating the composite image pixel with the corresponding pixel of the blood-flow image when blood flow is detected in the corresponding pixel of the blood-flow image.

13. The method of claim 11, wherein determining whether to use a corresponding pixel of the first resolution tissue structural image or a corresponding pixel of the blood-flow image to generate the composite image pixel comprises generating the composite image pixel with the corresponding pixel of the blood-flow image when the corresponding pixel of the blood-flow image has an energy level that exceeds a user-defined energy level.

14. A non-transitory computer-readable medium having processor-executable instructions for reading data from a processor in communication with at least one transducer disposed in a catheter, the processor-executable instructions when installed on a device enable the device to perform actions, comprising
receiving reflected echo signals corresponding to acoustic signals transmitted from the at least one transducer along each of a plurality of radial scan lines as the at least one transducer rotates about a longitudinal axis of the catheter;
passing the received echo signals through a plurality of first signal processing channels to form a plurality of filtered signals, the plurality of filtered signals comprising a first resolution tissue structure signal, a first blood-flow signal, and a second resolution tissue structure image signal, wherein the first resolution tissue structure signal has a resolution that is higher than a resolution of the second resolution tissue structure image signal, wherein each of the plurality of first signal processing channels comprises a different first filter, and wherein each of the received echo signals is passed through one of the different first filters;
processing the first resolution tissue structure signal and a plurality of additional first resolution tissue structure signals received from additional radial scan lines of the plurality of radial scan lines to generate a first resolution tissue structural image;
processing the first blood-flow signal and the second resolution tissue structure image signal with a plurality of additional first blood-flow signals received from additional radial scan lines of the plurality of radial scan lines to generate a blood-flow image that comprises at least one of a blood-flow velocity image, a blood-flow energy image, or a second resolution structural energy image; and
combining the first resolution tissue structural image with the blood-flow image to generate a composite image, for each pixel of the composite image, determining whether to use a corresponding pixel of the first resolution tissue structural image or a corresponding pixel of the blood-flow image to generate the composite image pixel.

15. The non-transitory computer-readable medium of claim 14, further comprising outputting the generated composite image to at least one display coupled to the device for displaying the composite image.

16. The non-transitory computer-readable medium of claim 14, wherein processing the first blood-flow signal and the second resolution tissue structure image signal with the plurality of second blood-flow signals received from additional radial scan lines of the plurality of radial scan lines to generate the blood-flow velocity image comprises forming the blood-flow velocity image based on the phase difference between the first blood-flow signal of the first radial scan line and at least one of the plurality of second blood-flow signals of at least one radial scan line of the plurality of radial scan lines that is adjacent to the first radial scan line.

17. The non-transitory computer-readable medium of claim 16, wherein processing the first blood-flow signal and the second resolution tissue structure image signal with the plurality of second blood-flow signals received from additional radial scan lines of the plurality of radial scan lines to generate the blood-flow energy image and the second resolution structural energy image comprises generating the blood-flow energy image and the second resolution structural energy image based, at least in part, on an amplitude of a calculated cross-correlation coefficient.

18. The non-transitory computer-readable medium of claim 17, wherein determining whether to use a corresponding pixel of the first resolution tissue structural image or a corresponding pixel of the blood-flow image to generate the composite image pixel comprises generating the composite image pixel with the corresponding pixel of the blood-flow image when blood flow is detected in the corresponding pixel of the blood-flow image.

19. A catheter-based imager comprising:
at least one transducer insertable into a catheter at least partially insertable into a patient, the at least one transducer coupled to a control module; and a processor in communication with the control module, the processor for executing processor-readable instructions that enable actions, including:
  receiving reflected echo signals corresponding to acoustic signals transmitted from the at least one transducer along each of a plurality of radial scan lines as the at least one transducer rotates about a longitudinal axis of the catheter,
  passing the received echo signals through a plurality of first signal processing channels to form a plurality of filtered signals, the plurality of filtered signals comprising a first resolution tissue structure signal, a first blood-flow signal, and a second resolution tissue structure image signal, wherein the first resolution tissue structure signal has a resolution that is higher than a resolution of the second resolution tissue structure image signal, wherein each of the plurality of first signal processing channels comprises a different first filter, and wherein each of the received echo signals is passed through one of the different first filters,
  processing the first resolution tissue structure signal and a plurality of additional first resolution tissue structure signals received from additional radial scan lines of the plurality of radial scan lines to generate a first resolution tissue structural image,
  processing the first blood-flow signal and the second resolution tissue structure image signal with a plurality of additional first blood-flow signals received from additional radial scan lines of the plurality of radial scan lines to generate a blood-flow image that comprises at least one of a blood-flow velocity image, a blood-flow energy image, or a second resolution structural energy image, and
  combining the first resolution tissue structural image with the blood-flow image to generate a composite image, for each pixel of the composite image, determining whether to use a corresponding pixel of the first resolution tissue structural image or a corresponding pixel of the blood-flow image to generate the composite image pixel.

20. The catheter-based imager of claim 19, further comprising outputting the generated composite image to at least one display coupled to the processor for displaying the composite image.

* * * * *